United States Patent [19]

Childers

[11] 4,335,112

[45] Jun. 15, 1982

[54] METHOD OF TREATING MITES IN POULTRY

[76] Inventor: Joseph R. Childers, 1123 N. Main St., Mocksville, N.C. 27028

[21] Appl. No.: 245,568

[22] Filed: Mar. 19, 1981

[51] Int. Cl.$^3$ ............................................. A61K 37/00
[52] U.S. Cl. ................................................... 424/177
[58] Field of Search ......................................... 424/177

[56] References Cited

U.S. PATENT DOCUMENTS 2,809,892 10/1957 Chornock ............................ 424/177

OTHER PUBLICATIONS

Singh et al., Chem. Abst., vol. 92, (1980), p. 105799V.

*Primary Examiner*—Sam Rosen
*Attorney, Agent, or Firm*—Charles R. Rhodes; Judith G. Smith

[57] ABSTRACT

The antibiotic bacitracin is introduced as a supplement into the feed for the poultry to control mites. The bacitracin is preferably administered by adding the zinc salt of bacitracin to the feed in amounts by weight in the range of 100–200 grams of bacitracin per ton.

5 Claims, No Drawings

METHOD OF TREATING MITES IN POULTRY

BACKGROUND AND SUMMARY OF THE INVENTION

The control and elimination of mites is a severe problem for poultry growers. For some unknown reason, mites appear periodically in a poultry grower's flock, and cause considerable discomfort to the poultry with the result that the poultry is less healthy, and less productive. Known methods of controlling or eliminating mites in poultry flocks generally include the introduction of a poison into a spray solution for the poultry. Oral ingestion of drugs is not known to the applicant as far as the control of mites is concerned.

One antibiotic, bacitracin has been used as a feed supplement by forming the zinc salt of bacitracin then removing the precipitated zinc bacitracin and waterinsoluable solids and drying the same to obtain the aforesaid feed supplement. The formulation of the feed supplement is disclosed and taught in U.S. Pat. to Chornock No. 2,809,892 issued Oct. 15, 1957, the teaching of which is incorporated herein by reference. As disclosed this feed supplement is utilized for the purpose of giving additional growth-promoting effects and aids in producing larger animals at an earlier age than can be done with feed containing only growth promoters such as vitamin $B_{12}$.

It is further known that bacitracin exhibits some additional beneficial results in the prevention and treatment of chronic respiratory diseases, egg production, egg hatchability, to prevent early mortality of baby chicks due to organisms sensitive to bacitracin, prevention and treatment of blue comb and for the suppression of secondary invaders that are sensitive to bacitracin during periods of stress, such as debeaking, vaccinating, and moving the flock. Known suggested portions of the active drug bacitracin range from 4 grams to 500 grams per ton.

Applicant of the instant invention, on the other hand, has found that this feed supplement has a separate and altogether unconnected use. This unique use is for the control and elimination of mites in poultry flocks. At the heart of this use is applicant's discovery that bacitracin is toxic to mites. It has been found that the introduction of this supplement into poultry grain in such amounts as to provide between 100 and 200 grams of bacitracin per ton for a short period of time (several days) will substantially eliminate mites from a flock of poultry so infested.

It is therefore within the objects of the present invention to provide a new and improved process for the elimination of mites in poultry flocks; which process involves causing the oral ingestion of the antibiotic bacitracin as by the introduction of the antibiotic bacitracin to the feed of the poultry.

Other objects and a fuller understanding of the invention will become apparent from reading the following detailed description of a preferred embodiment.

DETAILED DESCRIPTION OF A PREFERRED EMBODIMENT

As disclosed in the U.S. Pat. No. 2,809,892 the antibiotic bacitracin can be prepared as a feed supplement in any convenient method such as by precipitation from an aqueous solution by first dissolving ordinary bacitracin in water at about pH 5.0, adding zinc and adjusting the pH to about 7.0 to precipitate the zinc bacitracin. It can also be produced from an acidified aqueous concentrate of bacitrain by adding an aqueous solution of a water-soluble zinc salt such as zinc chloride, zinc sulphate, zinc acetate, etc., then raising the pH to precipitate the zinc bacitracin from the resulting solution.

As taught by the Chornock patent, when the zinc salt of bacitracin is employed to supplement a feed, there is employed a diluted solution of the zinc bacitracin to facilitate mixing the supplement in the feed. Some diluents which have been used include soy flour, finely ground wheat middlings, corn meal, etc. Other growth promoting materials such as vitamin $B_{12}$ etc., may be incorporated in the diluent along with the zinc salt of bacitracin. It is not important to the present invention how the zinc bacitracin is formed, or how it is mixed with the feed supplement, as long as the antibiotic bacitracin is orally ingested by the poultry. Preferably the bacitracin is added to the feed in such a manner as to provide 100-200 grams of bacitracin per ton of feed. More detailed information concerning the mixing of the zinc bacitracin with the feed and the initial forming of the zinc bacitracin may be obtained from a closer reading of the aforementioned U.S. Pat. No. 2,809,892.

The following example is offered to illustrate the manner in which the zinc bacitracin is used and the efficiency which it has realized. A flock of 10,000 Babcock chickens of an approximate age of 9-10 months, weighing approximately 3 pounds became heavily infested with mites. After use of zinc bacitracin formed as taught by the Chornock patent in the normal feed for the chickens in amounts of 100 grams per ton for a period of seven days, it was noticed that substantially all of the mites had disappeared. Ten months later the same flock again became mite infested. The same treatment was administered with the same effective results.

While one preferred embodiment for forming and mixing the antibiotic with the feed has been described in detail hereinabove, it is obvious that various changes might be made without departing from the scope of the invention. For example, while it does appear necessary to use at least 100 grams of zinc bacitracin per ton of feed, the upper end of the range is limited only by the economies of the situation. Therefore, the invention should be limited only by the claims below.

What is claimed is:

1. A method for eliminating mites in poultry infected with mites comprising administering the antibiotic bacitracin in an effective amount orally to the poultry.

2. The method according to claim 1 whereby the oral administration is effected by the introduction of a diluted solution of the zinc salt of said antibiotic bacitracin into poultry feed.

3. The method according to claim 2 wherein said bacitracin is added in an amount by weight at least equal to 100 grams per ton of feed.

4. A method for eliminating mites in poultry comprising supplementing the feed of the poultry with a diluted solution of the zinc salt of the antibiotic bacitracin and feeding the supplemented feed to the infected poultry.

5. The method according to claim 4 wherein the bacitracin is added in amounts by weight in the range of 100-200 grams per ton of feed.

* * * * *